(12) United States Patent
Choi

(10) Patent No.: US 9,549,789 B2
(45) Date of Patent: Jan. 24, 2017

(54) ORTHODONTIC BRACKET AND METHOD OF MANUFACTURING THE SAME

(71) Applicant: Jeng Soo Choi, Gyeonggi-do (KR)

(72) Inventor: Jeng Soo Choi, Gyeonggi-do (KR)

( * ) Notice: Subject to any disclaimer, the term of this patent is extended or adjusted under 35 U.S.C. 154(b) by 76 days.

(21) Appl. No.: 14/348,120

(22) PCT Filed: Mar. 5, 2013

(86) PCT No.: PCT/KR2013/001772
§ 371 (c)(1),
(2) Date: Mar. 28, 2014

(87) PCT Pub. No.: WO2013/157736
PCT Pub. Date: Oct. 24, 2013

(65) Prior Publication Data
US 2015/0037747 A1    Feb. 5, 2015

(30) Foreign Application Priority Data
Apr. 16, 2012    (KR) .......................... 10-2012-0039150

(51) Int. Cl.
| | |
|---|---|
| A61C 7/00 | (2006.01) |
| A61C 7/16 | (2006.01) |
| A61C 7/28 | (2006.01) |
| A61C 7/12 | (2006.01) |
| A61C 7/14 | (2006.01) |
| A61C 7/22 | (2006.01) |

(Continued)

(52) U.S. Cl.
CPC . *A61C 7/16* (2013.01); *A61C 7/12* (2013.01); *A61C 7/14* (2013.01); *A61C 7/22* (2013.01); *A61C 7/28* (2013.01); *A61C 7/303* (2013.01); *B23K 26/0066* (2013.01); *Y10T 29/49568* (2015.01)

(58) Field of Classification Search
CPC .................................... A61C 7/14; A61C 7/16
See application file for complete search history.

(56) References Cited

U.S. PATENT DOCUMENTS

| | | | |
|---|---|---|---|
| 4,430,061 A * | 2/1984 | Webb | A61C 7/16 433/9 |
| 4,604,057 A * | 8/1986 | Viglietti | A61C 7/16 433/9 |

(Continued)

FOREIGN PATENT DOCUMENTS

| | | |
|---|---|---|
| JP | 2010-042267 | 2/2010 |
| KR | 20060088206 | 8/2006 |

(Continued)

*Primary Examiner* — Ralph Lewis
(74) *Attorney, Agent, or Firm* — Novick, Kim & Lee, PLLC; Jae Youn Kim

(57) ABSTRACT

Disclosed is an orthodontic bracket and a method of manufacturing the same in which a bonding pattern is formed by irradiating a laser beam onto a base face of the orthodontic bracket that a machining process has been completed, and the bonding pattern formed on the base face is coated with an adhesive for attachment to teeth, thereby allowing the adhesive for attachment to teeth to firmly hold the orthodontic bracket on, and at the same time significantly reducing the processing time that takes to process the base surface for enabling for the adhesive to hold the orthodontic bracket on thereby enabling the mass production of the orthodontic bracket of high quality.

4 Claims, 7 Drawing Sheets

(51) Int. Cl.
A61C 7/30 (2006.01)
B23K 26/00 (2014.01)

(56) References Cited

U.S. PATENT DOCUMENTS

| | | | | | |
|---|---|---|---|---|---|
| 4,661,059 | A | * | 4/1987 | Kanno | A61C 7/16 433/9 |
| 5,820,371 | A | * | 10/1998 | Forster | A61C 7/12 433/9 |
| 5,944,517 | A | * | 8/1999 | Binder | A61C 7/16 433/23 |
| 6,910,884 | B2 | * | 6/2005 | Kelly | A61C 7/14 433/17 |
| 8,479,393 | B2 | * | 7/2013 | Abels | A61C 7/14 29/557 |
| 2010/0178628 | A1 | * | 7/2010 | Kim | A61C 7/12 433/10 |

FOREIGN PATENT DOCUMENTS

| KR | 20060097444 | 9/2006 |
|---|---|---|
| KR | 20080022881 | 3/2008 |
| KR | 20090090103 | 5/2009 |
| KR | 20100077765 | 7/2010 |
| KR | 20110042258 | 4/2011 |

\* cited by examiner

ORTHODONTIC BRACKET AND METHOD OF MANUFACTURING THE SAME

BACKGROUND

The present invention relates to an orthodontic bracket and a method of manufacturing the same in which a bonding pattern is formed by irradiating a laser beam onto a base face of the orthodontic bracket that a machining process has been completed, and the bonding pattern formed on the base face is coated with an adhesive for attachment to teeth, thereby allowing the adhesive for attachment to teeth to firmly hold the orthodontic bracket on, and at the same time significantly reducing the processing time that takes to process the base surface for enabling for the adhesive to hold the orthodontic bracket on thereby enabling the mass production of the orthodontic bracket of high quality.

In general, orthodontics means correcting dental abnormalities and should be targeted at an abnormality in the tissue around teeth, which causes poor alignment of the teeth, and includes adjusting an abnormality in occlusion in addition to the abnormality in the teeth alignment and correcting the so-called malocclusion such as prognathism of upper teeth and lower teeth.

The orthodontics uses braces for gradually moving teeth to correct the position of the tooth. The braces include brackets for straightening of irregular teeth and a wire having elasticity. In the braces, the bracket for straightening of irregular teeth is securely attached to a tooth face of a correction target tooth and the wire is fixed to the attached brackets for straightening of irregular teeth. The direction and magnitude of a force exerted on the arch wire can be adjusted variously by adjusting tension exerted on the arch wire, and the target teeth for treatment can be moved gradually while the direction and magnitude thereof is adjusted. The target teeth changes in its posture and position by the tension of the arch wire, and gradually moves little by little accordingly, thereby the orthodontics is made.

Korean Patent No. 0862631 as an example of such an orthodontic bracket discloses a method of manufacturing an orthodontic bracket for use in orthodontics, which is formed therein with a slot at one side thereof and an attaching face attached to a teeth face at the other side thereof, the attaching face of the bracket is provided with a lower portion to which polymer powders melted are attached so that an adhesive permeates gaps formed at lower ends of the polymer powders, wherein 20% to 30% of the polymer powders welded on the attaching face of the bracket is melted and welded on the attaching face and the wetting angle thereof is at 50° to 70°. The method includes a processing step in which a slot is formed at one side thereof and a bracket is formed with a attaching face at the other side thereof; a transparency diluting step of diluting a transparency thereof by abrasive blasting so that the reflectance of the bracket formed through the processing step is lowered; a powder welding step of welding the polymer powders onto the attaching face of the bracket formed through the processing step so that the adhesive permeates the gaps of the polymer powders welded on the bracket thereby maximizing adhesive efficiency.

Further, Korean Patent No. 1016416 discloses an orthodontic bracket for attaching a wire for exerting a force on tooth so that the teeth moves to a desired position, including a bracket body fixed to the wire and a detachably attaching means that is coupled to the bracket body and detachably attached to a teeth surface.

Further, Korean Patent No. 660646 discloses an orthodontic bracket including a main body being attached to tooth, a slot formed on one side of the main body to receive a wire, a coating layer formed on an opposite side of the main body, and a groove formed between the main body and the coating layer to increase the amount of coating material.

Further, Korean Patent No. 0763315 discloses an orthodontic bracket using an arch wire, including a bracket base fixed to a tooth surface, and a wire holder that is detachably mounted to the bracket base and fixed securely to the arch wire, wherein the arch wire is adjusted to exert a force on the tooth thereby moving the teeth to a predetermined position, and then solidly fixed to the wire holder.

The orthodontic bracket, which has been disclosed in Korean Patent No. 0763315 the inventor of which is the same as in the present invention, is provided with a coating layer for further improving an attachment force to an attachment surface. To make the coating layer formed on the attachment surface of the bracket, however, the process for the formation of the coating layer should include many complex steps such as coating alumina powder of more than 85% purity on the attachment surface of the orthodontic bracket, heating the bracket coated with alumina up to 1500° C.~1700° C. and then maintaining the upper most point of the heating temperature during 10~30 minutes, maintaining the attachment surface of the bracket coated with alumina at the upper most point of the temperature during 10~30 minutes and then leaving the bracket at a room temperature during a predetermined time to thereby cool the bracket, when the coating layer of alumina as an attachment surface of the bracket is formed after leaving the bracket at the room temperature during the predetermined time, checking the bracket to detect any defective coating layer of the bracket as to whether the coating layer of alumina is stably formed on the attachment surface of the bracket or whether the bracket is changed in its shape due to high temperature heating, and attaching the bracket to the teeth surface using a bonding material if the coating layer of alumina is formed on the attachment surface of the bracket through the detection process, etc. thus there are problems that the whole operation becomes very complex and it takes much time to manufacture the bracket.

SUMMARY OF THE INVENTION

To solve the above problems, an object of the present invention is to provide an orthodontic bracket and a method of manufacturing the same in which an adhesive pattern is formed by irradiating a laser beam onto a base face of the orthodontic bracket that a machining process has been completed, and then coated thereon with an adhesive for attachment to teeth, thereby allowing the adhesive to firmly hold the orthodontic bracket on, and at the same time significantly reducing the processing time that takes to process the base surface for enabling for the orthodontic bracket to hold the orthodontic bracket on thereby enabling the mass production of the orthodontic bracket of high quality.

To achieve the object of the present invention, the present invention provides an orthodontic bracket including a base face, which is formed at one side of the orthodontic bracket, coated with an adhesive for attachment to teeth to attach the orthodontic bracket to teeth; a bonding pattern that is formed on the base face by irradiating a laser beam onto the base face at a vertical angle or at a predetermined angle with respect to the base face so that the adhesive for attachment to teeth permeates the bonding pattern to hold the base face on thereby allowing the bracket to be fixed securely to the teeth; a slot into which a wire is inserted along a longitudinal direction at the center of a face of the orthodontic bracket, opposite to the base face; wings formed with a first wing and a second wing formed at both side faces of the orthodontic bracket; first side face groove and second side face groove that are formed oppositely each other at the centers of both side faces of the orthodontic bracket so as to divide the wings and base face so that a rubber ring is inserted thereto in order for the wire inserted into the slot not to get out of the slot; a wing division groove that is formed, at a right angle to the slot, on a face center on which the slot of the orthodontic bracket is formed so that the first wing and the second wing are divided into two, respectively, thereby each provided with a pair of the first wing and second wing; and a coupling groove provided at one end of the first wing of right side so that a rubber ring is coupled correspondingly thereto in state where the first wing of right side is formed longer than the first wing of left side among the pair of the first wings of right and left sides formed by the wing division groove.

Further, it is preferred that the base face is formed in a curved surface corresponding with a curved surface of teeth.

Further, it is preferred that the bonding pattern formed on the base face is formed with dent lines formed in a line throughout the base face.

Further, it is preferred that the dent lines are formed abreast or in a single file.

Further, it is preferred that the dent lines are formed in a line along a diagonal direction of the base face.

Further, it is preferred that the bonding pattern formed on the base face is formed in a lattice shape in which protrusions protrude from a recessed face of a base bottom throughout the base face, or a lattice shape in which protrusions protrude from a recessed face of a base bottom along a diagonal direction of the base face throughout the base face.

Further, it is preferred that the protrusions have any one shape selected from ○, ◇, □, ∆, ∇, ◁, ▷, ☆, and ○.

Further, it is preferred that the bonding pattern formed on the base face is formed in a shape in which holes are formed throughout the base face.

Further, it is preferred that the holes are formed in any one shape selected from ○, ◇, □, ∆, ∇, ◁, ▷, ☆, and ○.

The present invention provides a manufacturing method of an orthodontic bracket including a base face, which is formed at one side of the orthodontic bracket, coated with an adhesive for attachment to teeth to attach the orthodontic bracket to teeth; a bonding pattern that is formed on the base face by irradiating a laser beam onto the base face at a vertical angle or at a predetermined angle with respect to the base face so that the adhesive for attachment to teeth permeates the bonding pattern to hold the base face on thereby allowing the bracket to be fixed securely to the teeth; a slot into which a wire is inserted along a longitudinal direction at the center of a face of the orthodontic bracket, opposite to the base face; wings formed with a first wing and a second wing formed at both side faces of the orthodontic bracket; first side face groove and second side face groove that are formed oppositely each other at the centers of both side faces of the orthodontic bracket so as to divide the wings and base face so that a rubber ring is inserted thereto in order for the wire inserted into the slot not to get out of the slot; a wing division groove that is formed, at a right angle to the slot, on a face center on which the slot of the orthodontic bracket is formed so that the first wing and the second wing are divided into two, respectively, thereby each being provided with a pair of the first wing and second wing; and a coupling groove provided at one end of the first wing of right side so that a rubber ring is coupled correspondingly thereto in state where the first wing of right side is formed longer than the first wing of left side among the pair of the first wings of right and left sides formed by the wing division groove, the method includes a first step of setting, in a laser beam apparatus for processing, an irradiation angle of the laser beam relative to the base face, an irradiation depth of the laser beam relative to the base face and a bonding pattern shape of the base face to be processed in order to form the bonding pattern on the base face of the orthodontic bracket; and a second step of forming the bonding pattern on the base face by irradiating a laser beam from the laser beam apparatus onto the base face at a right angle or a predetermined angle with respect to the base face according to the irradiation angle of the laser beam relative to the base face, the irradiation depth of the laser beam relative to the base face and the bonding pattern shape of the base face to be processed, which are set in the laser beam apparatus.

Further, it is preferred that the bonding pattern is formed on the base face while heat generated in a processed portion of the base face is cooled, the processed portion is prevented from being burnt in black and the laser beam irradiated onto the base face is scattered, during processing of the bonding pattern by the laser beam apparatus after supplying a cutting material when the laser beam is irradiated onto the base face in the second step.

Further, it is preferred that the cutting material is any one selected from water, hand cream, and cutting oil.

Further, it is preferred that the bonding pattern formed on the base face is formed with dent lines formed in a line throughout the base face.

Further, it is preferred that the dent lines are formed abreast or in a single file.

Further, it is preferred that the dent lines are formed in a line along a diagonal direction of the base face.

Further, it is preferred that the bonding pattern formed on the base face is formed in a lattice shape in which protrusions protrude from a recessed face of a base bottom throughout the base face, or a lattice shape in which protrusions protrude from a recessed face of a base bottom along a diagonal direction of the base face throughout the base face.

Further, it is preferred that the protrusions have any one shape selected from ○, ◇, □, ∆, ∇, ◁, ▷, ☆, and ○.

Further, it is preferred that the bonding pattern formed on the base face is formed in a shape in which holes are formed throughout the base face.

Further, it is preferred that the holes are formed in any one shape selected from ○, ◇, □, ∆, ∇, ◁, ▷, ☆, and ○.

The present invention provides an orthodontic bracket and a method of manufacturing the same in which an adhesive pattern is formed by irradiating a laser beam onto a base face of the orthodontic bracket that a machining process has been completed, and then coated thereon with an adhesive for attachment to teeth, thereby allowing the adhesive to firmly hold the orthodontic bracket on, and at the same time significantly reducing the processing time that takes to process the base surface for enabling for the orthodontic bracket to hold the orthodontic bracket on thereby enabling the mass production of the orthodontic bracket of high quality.

DETAILED DESCRIPTION OF PREFERRED EMBODIMENTS

Hereinafter, the orthodontic bracket according to the present invention will be described with reference to the accompanying drawings.

FIGS. 1 to 5 show each bonding pattern formed on a base face according to the present invention. As shown, the orthodontic bracket according to the present invention is formed with various type of bonding pattern 20 on a base face 11 coated with an adhesive for attachment to teeth to attach the orthodontic bracket to the teeth.

Figure 1:
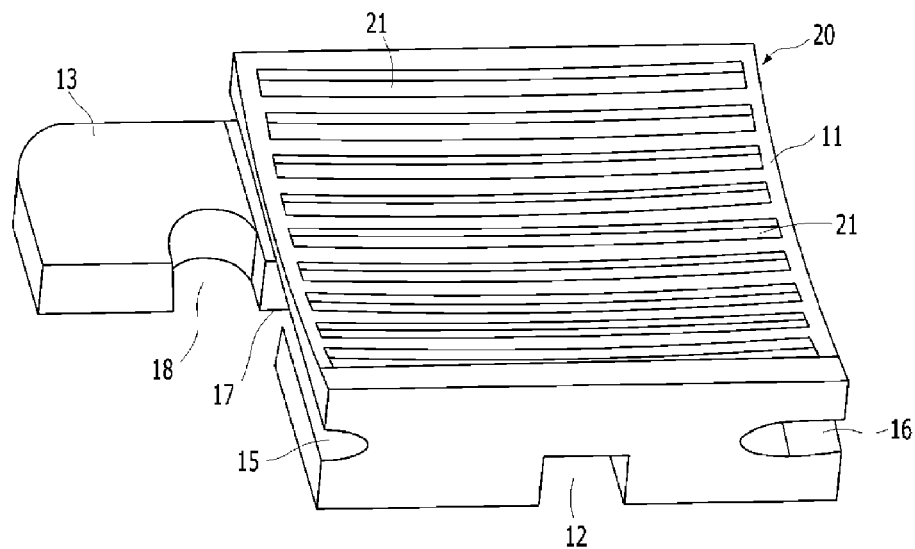
FIGS. 1 to 5 show each bonding pattern formed on a base face according to the present invention.
Figure 2:
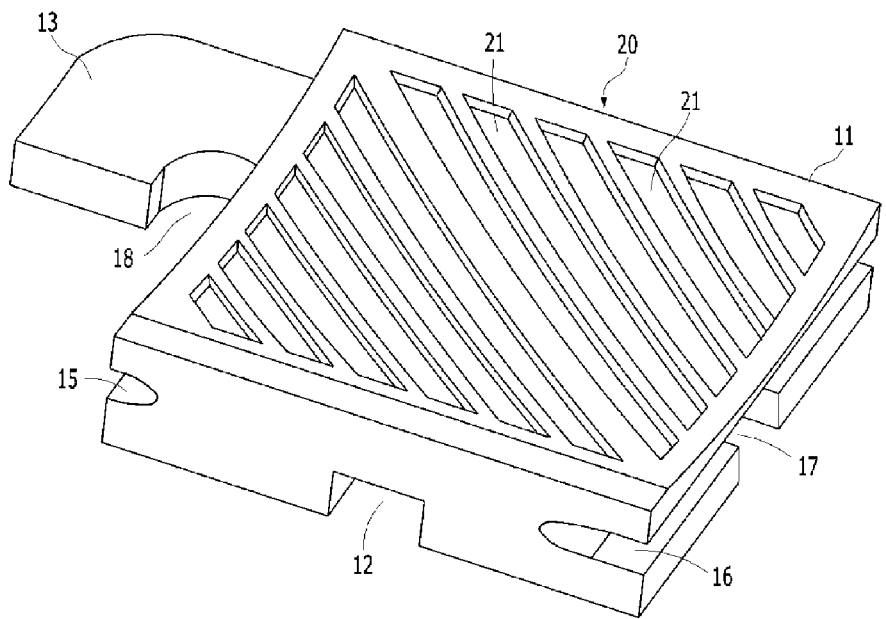

In more detail, as shown in FIGS. 1 and 2, the bonding pattern may be formed in a shape of the dent line 21 throughout the base face 11. That is, as shown in FIG. 1, the dent lines 21 may be formed abreast or in a single file in the base face 11 so that the bonding pattern 20 is formed horizontally with respect to four corners of the base face 11 of rectangular shape. Further, as shown in FIG. 2, the bonding pattern 20 may be formed in such a manner that the dent lines 21 are formed in a line in the base face 11 along the diagonal direction of the base face 11 of rectangular shape.

When the bonding pattern 20 is formed, the edges of the base face 11 are formed to correspond with the base face 11 and the dent lines 21 are formed in a shape of being recessed in the edges of the base face 11. Since the edges of the base face 11 corresponding with such base face 11 serve to prevent the adhesive permeating the dent line 21 from getting out of the base face 11, it is possible to prevent any inconvenience that an excessive adhesive should be removed, which flows onto a tooth surface beyond the base face 11 after the orthodontic bracket has been installed.

The bonding pattern 20, which is formed in a shape of the dent lines 21 that is in a horizontal position with respect to the four corners of the base face 11 of a rectangular shape, is very simple in the process as compared with the other bonding pattern 20, thereby making it possible to fast manufacture its product, thus the product is suitable for mass production.

The bonding pattern 20 shown in FIG. 2, which is formed in a shape of the dent line 21 formed in a diagonal direction of the base face 11, serves to prevent the base face from sliding on the teeth surface as compared with the bonding pattern 20 having the dent lines 21 arranged in parallel line, because the adhesive for attachment to teeth permeating the dent line 20 along the diagonal direction is attached to the teeth in the diagonal direction with respect to a tooth surface, thereby making it easy to attach the bonding face to the tooth surface.

Of course, in the case where the width of the dent line 21 is widened or deepened, since the area where the adhesive for attachment to teeth permeates is widened, it is possible to improve the adhesion strength of the adhesive.

Figure 3:
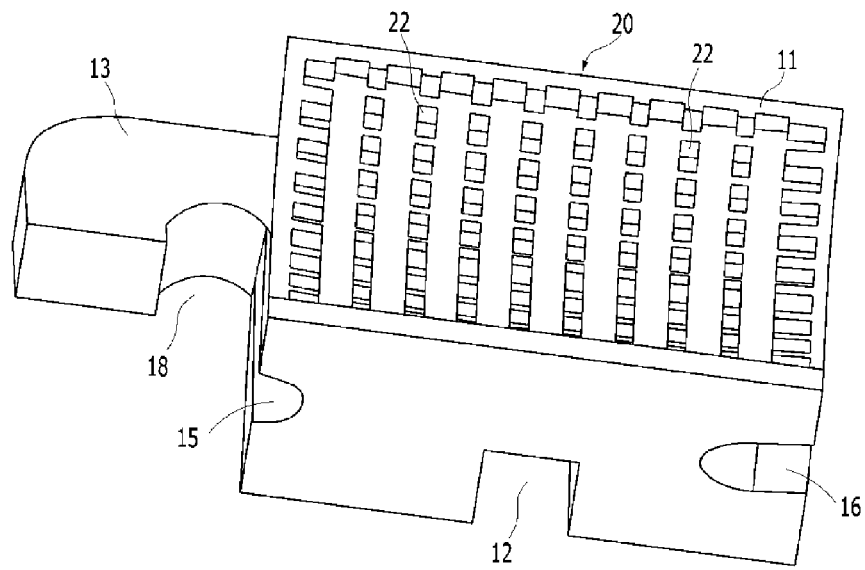
Figure 4:
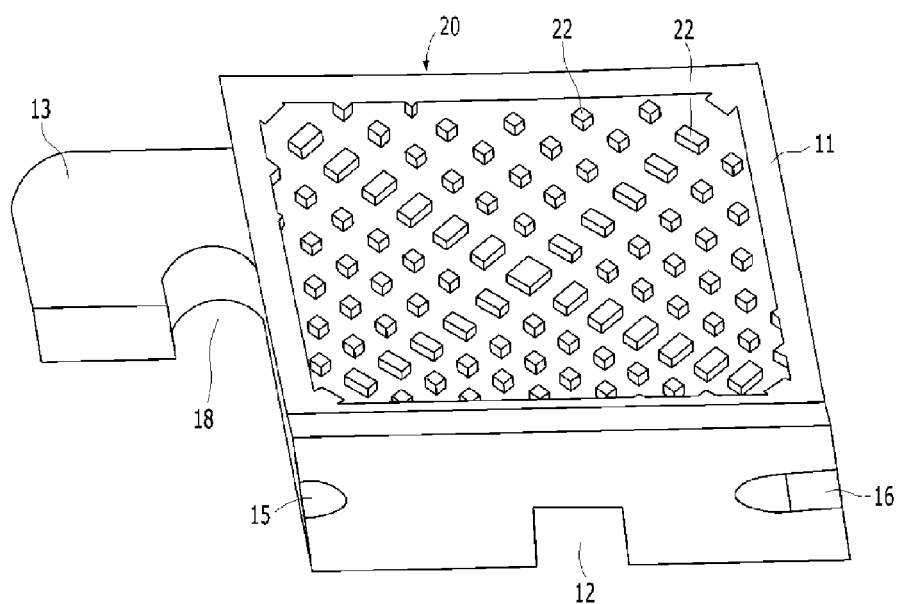

The bonding pattern 20 shown in FIGS. 3 and 4 may be formed in a lattice shape in which protrusions 22 protrude from the dent face 23 of the base bottom throughout the base face 11 of a rectangular shape. That is, the bonding pattern 20, as shown in FIG. 3, is provided with the protrusions 22 that are arranged in a lattice shape throughout the base face 11 so as to be in a horizontal position with respect to the four corners of the base face 11. In the bonding pattern 20 shown in FIG. 4, the protrusions 22 are formed in a lattice shape in the base face 11 along the diagonal direction of the base face 11 having a rectangular shape.

When the bonding pattern 20 is formed, the edges of the base face 11 is formed to coincide with the base face 11 and then the protrusions 22, which protrude from the dent face 23 of the base bottom, are formed at the inner side of the edges of the base face 11. Since the edges of the base face 11, which coincide with such base face 11, serve to prevent the adhesive permeating the gap between the protrusions 22 formed throughout the base face 11 from getting out of the base face 11, it is possible to prevent any inconvenience caused by removing of an excessive adhesive flowing onto a tooth surface beyond the base face 11 after the orthodontic bracket has been installed on the teeth.

The bonding pattern 20 shown in FIG. 3, in which the protrusions 22 are formed in a lattice shape throughout the base face 11 so as to be in a horizontal position with the four corners of the base face 11, allows the orthodontic bracket to be fixed solidly to the teeth because the adhesive for attachment to teeth permeates the gap between the protrusions 22 as well as the surface of the protrusions 22.

The bonding pattern 20 shown in FIG. 4, in which the protrusions 22 are formed in a lattice shape along the diagonal direction of the base face 11 at the inner side of the base face 11, less slides on the tooth surface as compared with the bonding pattern of a lattice shape thereby less moving and accordingly making it easy to attach to the tooth surface, because the adhesive permeating the gap between the protrusions 22 as well as the faces of the protrusions 22 is attached in the diagonal direction with respect to the surface of the tooth.

It is preferred that the top face of the protrusion 22 is formed in a protruded shape from the dent face 23 of the base bottom so as to coincide with the base face 11. Of course, the protrusions 22 may be formed in different shapes, in a larger shape in the size, or may be increased in its number, thereby making the bonding area of the adhesive widened, and accordingly making the bonding strength increased.

It is most preferable that the protrusions 22 are formed in a rectangular shape such as □ for easy processing, but the protrusions 22 may be formed in shapes such as ○, ◇, □, △, ▽, ◁, ▷, ☆, and ○ in consideration of adhesion strength and design.

Figure 5:
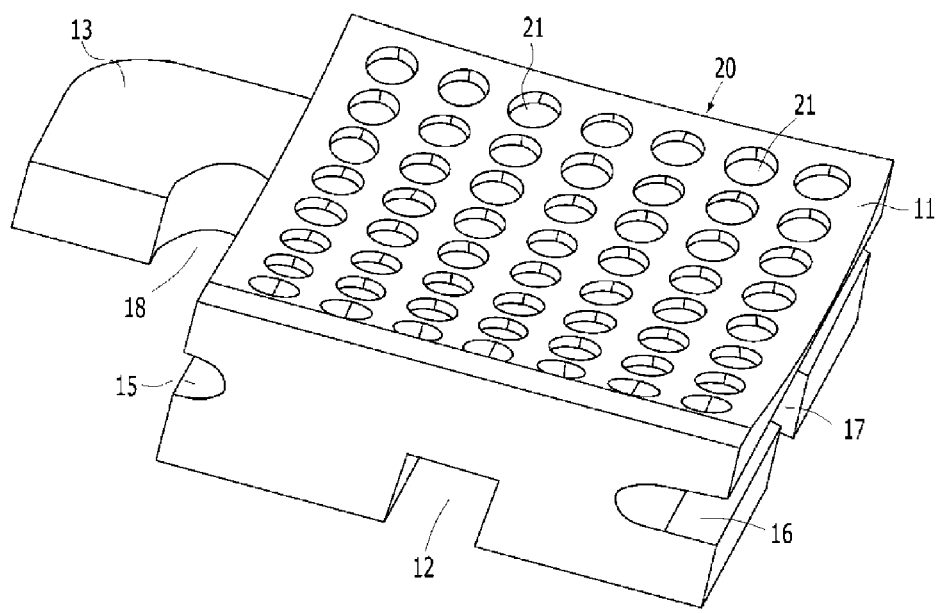

The bonding pattern 20 shown in FIG. 5 may be formed with the holes 24 throughout the base face 11. In detail, the holes 24 are formed throughout the base face 11 so that the holes have a constant depth from the base face 11. The holes 24 are arranged in a regular shape at regular intervals throughout the base face 11, or in an irregular shape.

When the bonding pattern 20 having the holes 24 as shown in FIG. 5 catches light in the state where the bracket is attached to teeth, the holes 24 absorb the light thereby maximizing the degree of clearness and enabling to solve the flaw of an existing orthodontic bracket that is easily visible to the naked eye due to glittering phenomenon caused by the reflection of light on the orthodontic bracket.

Of course, the holes 24 may be formed in different shapes, in a larger shape in the size, or may be increased in its number, thereby making the bonding area of the adhesive widened, and accordingly making the bonding strength increased.

It is most preferable that the holes 24 are formed in a circular shape such as ○ for easy processing, but the holes 24 may be formed in shapes such as, ◇, □, △, ▽, ◁, ▷, ☆, and ◯ in consideration of adhesion strength and design.

Figure 6:
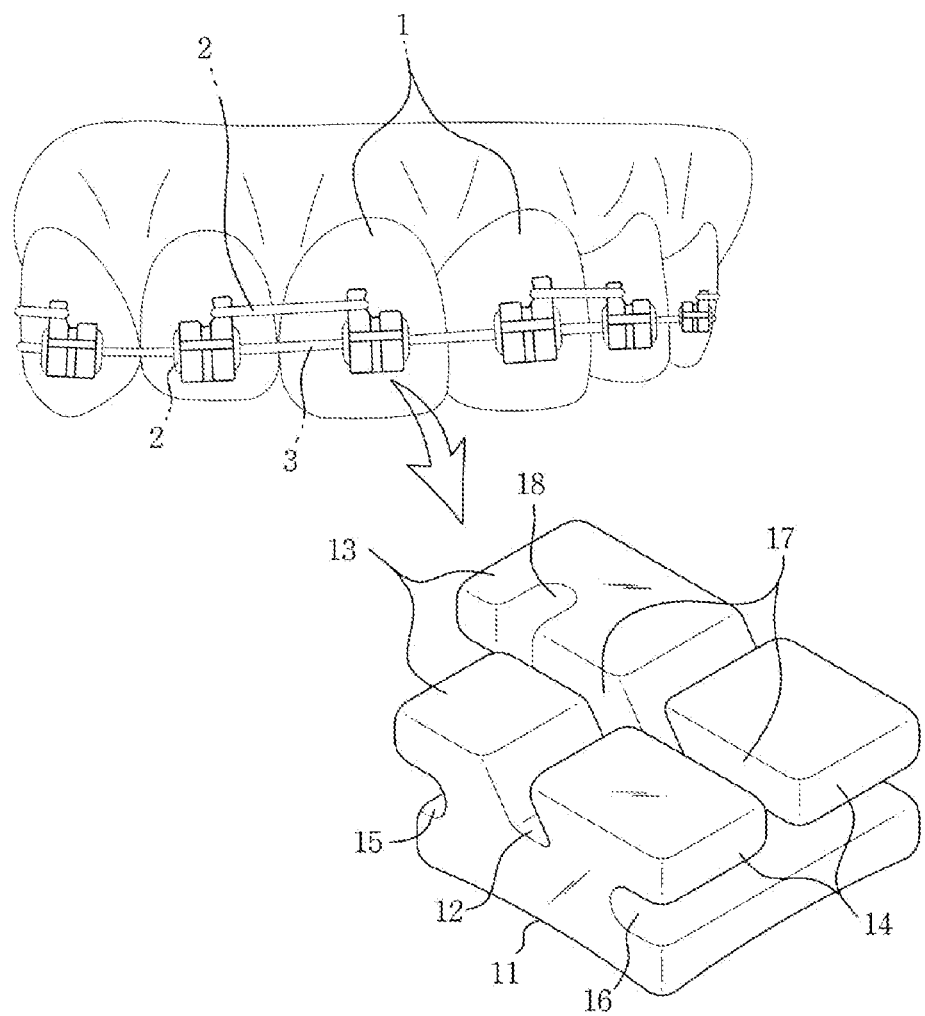
FIG. 6 is a configuration view showing an orthodontic bracket according to the present invention.

FIG. 6 shows a configuration of the orthodontic bracket. As depicted in the drawing, the orthodontic bracket according to the present invention includes a base face 11 that is formed at one side of the orthodontic bracket and formed thereon with a bonding pattern 20 coated with an adhesive for attachment to teeth to attach the orthodontic bracket to teeth; a slot 12 that is formed at the center of an upper side of the orthodontic bracket so that a wire 3 is coupled thereto; wings having a first wing 13 and a second wing 14 that are formed at both sides of the upper and lower portions of the orthodontic bracket formed therein with the slot 12; first side face groove 15 and second side face groove 16 that are formed oppositely each other at the centers of both sidefaces of the orthodontic bracket so as to divide the wings and base face 11 so that a rubber ring 2 is inserted thereinto in order for the wire inserted into the slot not to get out of the slot 12; a wing division groove 17 that is formed, at a right angle to the slot 12, on a face center on which the slot 12 of the orthodontic bracket is formed so that the first wing 13 and the second wing 14 are divided into two, respectively, thereby each being provided with a pair of the first wing 13 and second wing 14; and a pair of wings 13 formed at left and right sides by the wing division groove 17. At this time, the first wing 13 at right side is formed longer than the first wing 13 of left side among the pair of the first wings 13 formed at right and left sides. A coupling groove 18 is provided at one end of the first wing 13 of right side so that a rubber ring 2 is coupled correspondingly thereto.

It is preferable that the base face 11 is formed in a curved surface to coincide with a tooth face so that the base face 11 is adhered closely to the teeth 1 having a curved surface in state being coated with the adhesive.

The method of correcting the misalignment of teeth by using the orthodontic bracket according to the present invention will be described as follows with reference to FIG. 6. First, if the base face 11 of the orthodontic bracket is coated with the adhesive and then coagulated after a lapse of a predetermined time, the orthodontic bracket is attached to one end of the teeth 1 to be corrected.

Next, the position of the orthodontic bracket is arranged so that the wire 3 is easily inserted thereinto. If the adhesive semi-solidified is fully solidified after a lapse of a predetermined time, the wire 3 is inserted into the slots 12 of the numerous orthodontic brackets attached to the teeth 1.

When the base face 11 is coated with the adhesive for attachment to teeth, the adhesive naturally permeates the bonding pattern 20 such as the dent lines 21, protrusions 22, holes 24 or the like formed on the base face 11, and then the orthodontic bracket is adhered closely to the teeth 1 by making the base face 11 coated with the adhesive face the teeth. As a result, the orthodontic bracket can solidly be attached to the teeth 1 because the adhesive is adhered strongly to the bonding pattern 20.

And, the rubber ring 2 is insertion-coupled to the first and second side faces grooves 15, 16 of the orthodontic bracket in order for the wire 3 not to get out of the slot 12 of the orthodontic bracket, and at the same time, the rubber ring 2 is insertion-coupled to the coupling groove 18 formed in the right side first wing 13 of another orthodontic bracket which is adjacent to the coupling groove 18 formed in the right side first wing 13 of longer than the left side first wing 13 of the orthodontic bracket attached to the teeth 1.

As such, if the rubber ring 2 is coupled to the coupling grooves 18 of both the orthodontic brackets, the rubber ring 2 pulls inwards the coupling grooves 18 of both the orthodontic brackets attached to the teeth 1 thereby narrowing a gap between two adjacent tooth 1 to straight the irregular teeth.

Next, the method of manufacturing the orthodontic bracket according to the present invention will be described with reference to the accompanying drawings.

Figure 7:
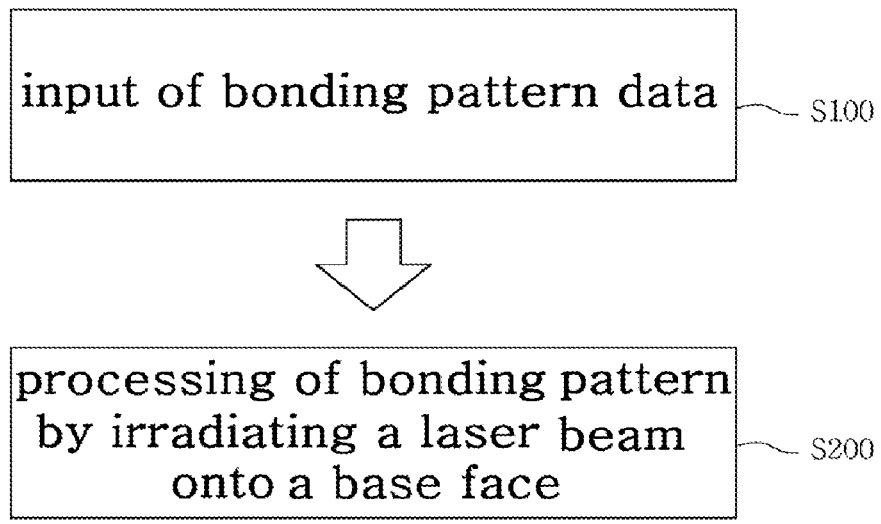
FIG. 7 is a flow chart illustrating a method of manufacturing the orthodontic bracket according to the present invention.

FIG. 7 is a flow chart showing the order of the manufacturing method of the orthodontic bracket. The manufacturing method of the orthodontic bracket according to the present invention includes a first step S100 of inputting processing information on the bonding pattern 20 of the base face 11 of the orthodontic bracket to be processed to a processing program installed in the processing laser beam apparatus 30, and a second step S200 of forming the bonding pattern 20 on the base face 11 on the basis of the processing program to which the processing information has been input in the first step. The detailed steps are as follows.

(1) First step: input of the processing information on the bonding pattern formed on the base face.

The first step S100 is a step of inputting, to a processing program of the processing laser beam apparatus 30, the processing information on an irradiation angle of the laser beam 31, an irradiation depth of the laser beam 31 from the base face 11, a shape of the bonding pattern 20 to be formed on the base face 11 or the like, in order to form the bonding pattern 20 on the base face 11 of the orthodontic bracket to be processed.

(2) Second step: formation of the bonding pattern on the base face.

The second step S200 is a step of forming the bonding pattern 20 such as the dent line 21, protrusions 22, holes 24 and the like on the base face 11, as shown in FIGS. 1 to 5, by irradiating the laser beam 31 at a right angle or at a predetermined angle with respect to the base face on the basis of the processing information that has been inputted in advance to the program of the processing laser beam apparatus 30 in the first step S100.

Figure 8:
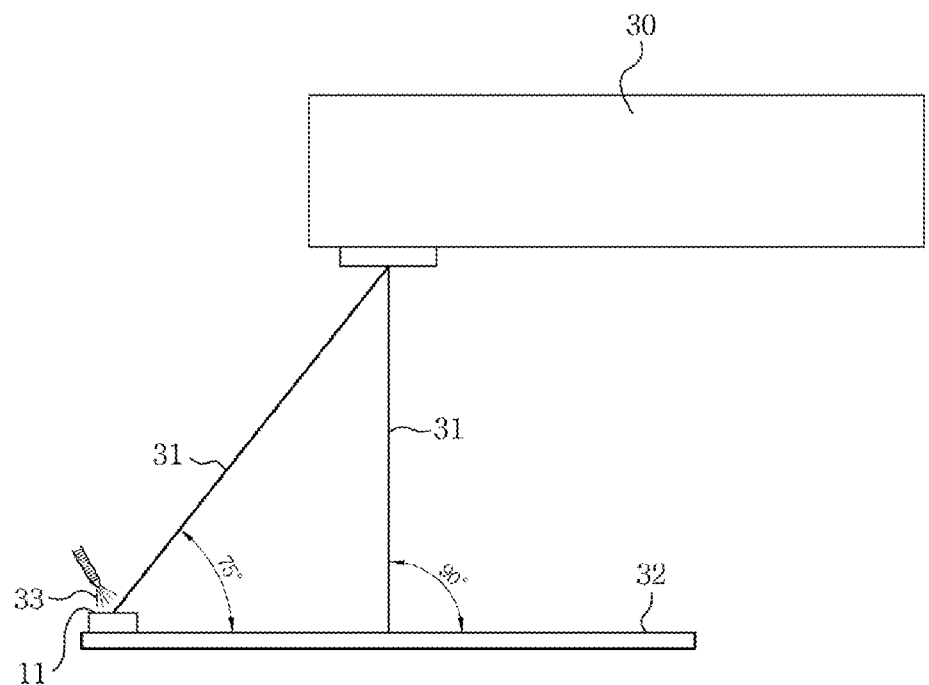
FIGS. 8 and 9 show processes of processing the bonding pattern by irradiating a laser beam onto the base face in a laser beam apparatus for processing according to the present invention.

Here, as shown in FIG. 8, the orthodontic bracket is installed in such a manner that the irradiation angle of the laser beam 31 forms a right angle with respect to the base face 11 and the base face 11 is in a horizontal position with the processing table 32, and then the bonding pattern 20 is processed to have the patterns such as the dent line 21, protrusions 22, holes 24 and the like as shown in FIGS. 1 to 5.

Incidentally, when the bonding pattern 20 is formed by forming the dent lines 21, protrusions 22, and holes 24 in an undercut shape, the bonding pattern 20 is processed more deeply than when being formed by irradiating the laser beam 31 at a right angle with respect to the base face 11. Furthermore, if the thus formed gap is filled with the adhesive and the adhesive is solidified, superior adhesive strength between the orthodontic bracket and the teeth may be demonstrated.

Figure 9:
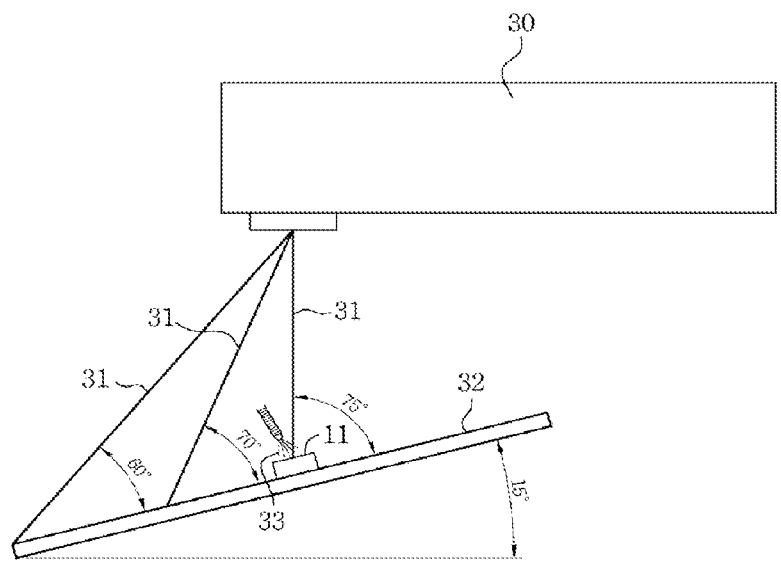

In another embodiment, as shown in FIG. 9, the orthodontic bracket is installed on the processing table 32 that is tilted with respect to a horizontal face, and then the bonding pattern 20 may be processed to have the patterns such as the dent line 21, protrusions 22, holes 24 and the like as shown in FIGS. 1 to 5 by irradiating the laser beam 31 at a right angle or an acute angle less than 90 degrees with respect to the base face 11.

Meanwhile, when the bonding pattern 20 is processed on the base face 11 by irradiating the laser beam 31 thereon, since the processed face may be burnt by heat generated in a processed portion of the base face 11, it is preferable that the processing target face is processed while the cutting material 33 for cooling the heat is sprayed onto the base face to be processed. As such cutting material 33, it is preferable to use water, hand cream harmless to humans even though contacted with the orthodontic bracket, or cutting oil generally used for processing.

When the laser beam 13 is irradiated on the base face 11 that has been dried directly at the work place, a phenomenon the processed portion is burnt in black is occurred while the circular holes 24 are formed on the base face 11 during processing of the bonding pattern 20 such as the holes 24 as shown in FIG. 6. When the bonding pattern 20 such as the holes shown in FIG. 6 is processed on the base face 11 while the cutting material 33 is sprayed onto the base face 11, however, the holes 24 are formed in a hexagonal shape such as ⬡ on the base face 11 without such a burning phenomenon on the processed portion because the cutting material 33 serves to scatter the laser beam 3. Such hexagon shaped holes 24 have wider areas to be filled with the adhesive than those of the circular holes 24 thereby improving the adhesive strength thereof.

Next, the detailed processing of the bonding pattern according to the embodiment will be described as follows.

First Embodiment

Processing of the Bonding Pattern Such as the Horizontal Dent Lines Shown in FIG. 1

The dent lines 21 are processed abreast or in a single file in the base face by irradiating the laser beam onto the base face. In more detail, the dent lines 21 consist of 3 to 30 dent lines each of which is about 0.2 to 1.0 mm in width and 0.2 to 1.5 mm in depth. Convex lines having the width of about 0.2 to 1.0 mm and the height of about 0.2 to 1.5 mm are also formed between the dent lines. The base face is irradiated at a right angle or an acute angle with the laser beam for the processing of the dent lines. The dent lines are formed in a U like concave shape or V like concave shape.

The bonding pattern according to the first embodiment can be fastest manufactured because of its simplest shape as compared with the other things. The wider the width of the dent line and the deeper the depth of the dent line are formed, the more the adhesive permeates the dent line, thereby enabling the adhesive strength to be increased.

Second Embodiment

Processing of the Bonding Pattern Such as the Diagonal Dent Lines Shown in FIG. 2

The dent lines 21 are processed in a diagonal direction in the base face by irradiating the laser beam onto the base face. In more detail, the dent lines 21 are processed to thereby consist of 3 to 30 dent lines each of which is about 0.2 to 1.0 mm in width and 0.2 to 1.5 mm in depth. Convex lines having the width of about 0.2 to 1.0 mm and the height of about 0.2 to 1.5 mm are also formed between the dent lines. The base face is irradiated at a right angle or an acute angle with the laser beam for the processing of the dent lines. The dent lines are formed in a U like concave shape or V like concave shape.

Since the bonding pattern according to the second embodiment is formed in the diagonal direction, the orthodontic bracket less moves on the teeth when the orthodontic bracket is attached to the teeth after being coated with the adhesive thereby making it easy for the orthodontic bracket to be attached to the teeth. The wider the width of the dent line and the deeper the depth of the dent line are formed, the more the adhesive permeates the dent line, thereby enabling the adhesive strength to be increased.

Third Embodiment

Processing of the Bonding Pattern Such as the Horizontal Protrusions Shown in FIG. 3

The protrusions are processed abreast or in a single file in the base face by irradiating the laser beam onto the base face. The protrusions consist of 1 to 200 protrusions each of which is about 0.1 to 1.0 mm in width and 0.2 to 1.5 mm in depth. The laser beam is irradiated at a right angle or an acute angle onto the base face for the processing of the protrusions. The protrusions are formed in the shape of ○, ◇, □, △, ▽, ◁, ▷, ☆, ◯, etc.

The bonding pattern according to the third embodiment enables the adhesive to be confined by the protrusions formed throughout the base face. The larger the size of the protrusion and the more the number of the protrusions are formed, the wider the coated area of the adhesive is, thereby enabling the adhesive strength to increase.

Fourth Embodiment

Formation of the Bonding Pattern Such as the Diagonally Arranged Protrusions Shown in FIG. 4

The protrusions are processed in a diagonal direction in a line in the base face by irradiating the laser beam onto the base face. The protrusions are processed to consist of 1 to 200 protrusions each of which is about 0.1 to 1.0 mm in width and 0.2 to 1.5 mm in depth. The laser beam is irradiated at a right angle or an acute angle onto the base face for the processing of the protrusions. The protrusions are formed in the shape of ○, ◇, □, △, ▽, ◁, ▷, ☆, ◯, etc.

The bonding pattern according to the fourth embodiment enables the adhesive to be confined by the protrusions formed throughout the base face. The larger the size of the protrusion and the more the number of the protrusions are formed, the wider the coated area of the adhesive is, thereby enabling the adhesive strength to increase. Since the bonding pattern according to the second embodiment is formed in the diagonal direction, the orthodontic bracket less moves on the teeth when the orthodontic bracket is attached to the teeth after being coated with the adhesive, thereby making it easy for the orthodontic bracket to be attached to the teeth.

Fifth Embodiment

Processing of the Bonding Pattern Such as the Holes Shown in FIG. 5

The holes are processed throughout the base face by irradiating the laser beam onto the base face. The holes are processed to consist of 1 to 200 holes each of which is about 0.1 to 1.0 mm in width and 0.2 to 1.5 mm in depth. The laser beam is irradiated at a right angle or an acute angle onto the base face for the processing of the holes. The holes are formed in the shape of ○, ◇, □, ∆, ∇, ◁, ▷, ☆, ◯, etc.

When the bonding pattern 20 according to the fifth embodiment catches light in the state where the bracket is attached to teeth, the holes absorb the light thereby maximizing the degree of clearness and enabling to solve the flaw of an existing orthodontic bracket that is easily visible to the naked eye due to glittering phenomenon caused by the reflection of light on the orthodontic bracket. The larger the size of the holes and the more the number of the holes are formed, the wider the coated area of the adhesive is, thereby enabling the adhesive strength to increase.

Fifth Embodiment

Adhesive Strength of Each Bonding Pattern According to the Irradiation Angles of the Laser Beam

TABLE 1

(Adhesive strength of bonding pattern of dent line according to irradiation angle of laser beam)

| NO. of test | Bonding pattern of dent line (10°) | | Bonding pattern of dent line (15°) | | Bonding pattern of dent line (20°) | |
| --- | --- | --- | --- | --- | --- | --- |
| | Unit: N | Unit: MPa | Unit: N | Unit: MPa | Unit: N | Unit: MPa |
| 1 | 74.5 | 7.10 | 64.6 | 6.15 | 29.2 | 2.78 |
| 2 | 123.4 | 11.75 | 166.6 | 15.87 | 5.3 | 0.50 |
| 3 | 62.6 | 5.96 | 103 | 9.71 | 13.4 | 1.28 |
| 4 | 48 | 4.57 | 114.1 | 10.87 | 99.2 | 9.45 |
| 5 | 66.6 | 6.34 | 45.5 | 4.33 | 20.9 | 1.99 |
| 6 | 49.2 | 4.69 | 84.8 | 8.08 | 34.4 | 3.28 |
| 7 | 109 | 10.38 | 100.6 | 9.58 | 19.1 | 1.82 |
| 8 | 50.6 | 4.82 | 137.3 | 13.08 | 11.7 | 1.11 |
| 9 | 87.9 | 8.37 | 99.9 | 9.51 | 60.5 | 5.76 |
| 10 | 63.3 | 6.03 | 84.5 | 8.05 | 38.8 | 3.65 |
| 11 | 61.9 | 5.90 | 53.3 | 5.08 | 30.8 | 2.93 |
| 12 | 72.9 | 6.94 | 87.9 | 8.37 | 6.3 | 0.60 |
| 13 | 74.7 | 7.11 | 46.9 | 4.47 | 65.2 | 6.21 |
| 14 | 36.4 | 3.47 | 69.8 | 6.65 | 25.6 | 2.44 |
| 15 | 100.7 | 9.59 | 77 | 7.33 | 5.3 | 0.50 |
| Average | 72.11333 | 6.87 | 88.98667 | 8.47 | 31.01333 | 2.95 |

Figure 10:
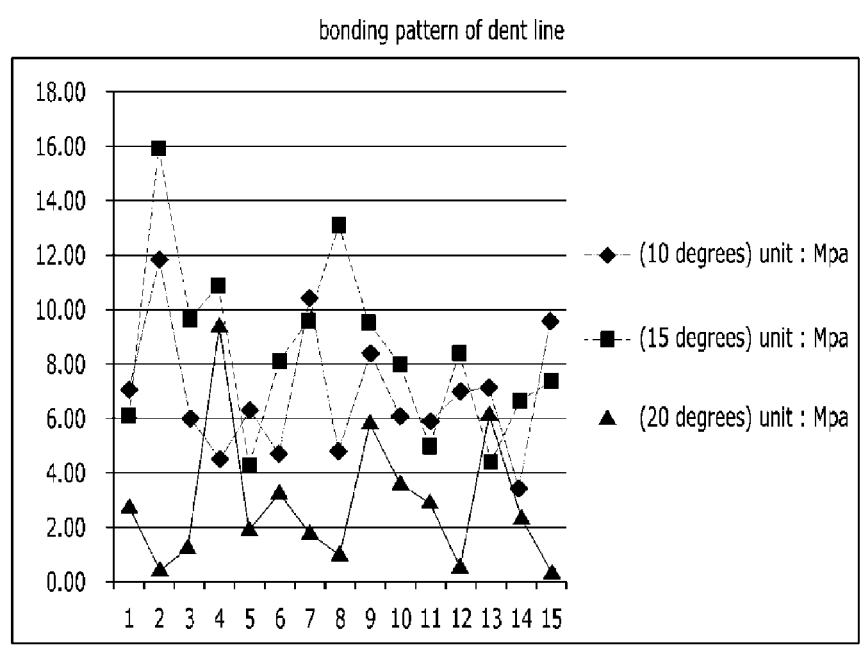
FIGS. 10 to 12 are graphs for comparing bonding strengths of the bonding patterns formed on the base face according to the irradiation angles of a laser beam according to the present invention.

As shown in FIGS. 8 and 9, the bonding pattern such as the dent line is formed on the base face by irradiating the laser beam onto the base face at angles of 10°, 15° and 20°. In the case of the bonding pattern of the dent line, as shown in table 1 and FIG. 10, when the bonding pattern such as the dent line is formed on the base face by irradiating the laser beam at an angle of 15° with respect to the base face, the average adhesive strength is 8.47 Mpa (88.98667N), which indicates that the adhesive strength of the adhesive is strongest.

TABLE 2

(Adhesive strength of bonding pattern of protrusion according to irradiation angle of laser beam)

| NO. of test | Bonding pattern of protrusion (10°) | | Bonding pattern of protrusion (15°) | | Bonding pattern of protrusion (20°) | |
| --- | --- | --- | --- | --- | --- | --- |
| | Unit: N | Unit: MPa | Unit: N | Unit: MPa | Unit: N | Unit: MPa |
| 1 | 195.7 | 18.64 | 72.6 | 6.91 | 119.7 | 11.40 |
| 2 | 109.1 | 10.39 | 84.3 | 8.03 | 114.1 | 10.87 |
| 3 | 142.3 | 13.55 | 190.4 | 18.13 | 49.8 | 4.74 |
| 4 | 171.3 | 16.31 | 107.7 | 10.26 | 94.1 | 8.96 |
| 5 | 116.1 | 11.06 | 56.3 | 5.36 | 117 | 11.14 |
| 6 | 110 | 10.48 | 142.8 | 13.60 | 252.1 | 24.01 |
| 7 | 95.1 | 9.06 | 71.51 | 6.81 | 149.1 | 14.20 |
| 8 | 111.5 | 10.62 | 99.8 | 9.50 | 117.7 | 11.21 |
| 9 | 147.9 | 14.09 | 90.6 | 8.63 | 99.3 | 9.46 |
| 10 | 142.1 | 13.53 | 94.7 | 9.02 | 118.5 | 11.29 |
| 11 | 86.6 | 8.25 | 145 | 13.81 | 115 | 10.95 |
| 12 | 142.4 | 13.56 | 171.2 | 16.30 | 124.4 | 11.85 |
| 13 | 169.6 | 16.15 | 123.5 | 11.76 | 131.2 | 12.50 |
| 14 | 192.8 | 18.36 | 110.9 | 10.56 | 149.7 | 14.26 |
| 15 | 132.7 | 12.64 | 127.2 | 12.11 | 133.8 | 12.74 |
| Average | 137.68 | 13.11 | 112.5667 | 10.72 | 125.7 | 11.97 |

Figure 11:
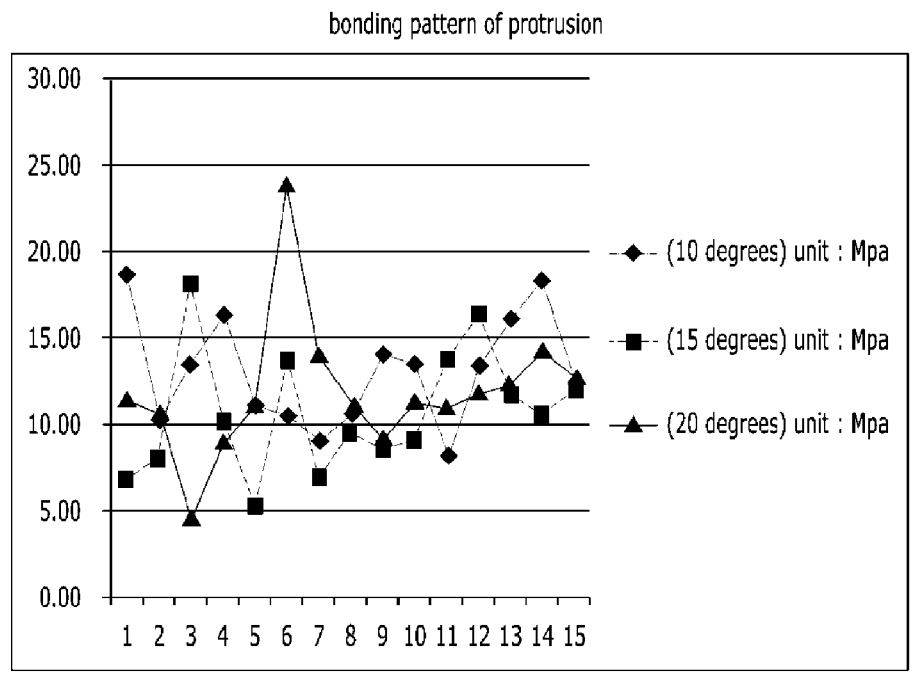

As shown in FIGS. 8 and 9, the bonding pattern such as the protrusions is formed on the base face by irradiating the laser beam onto the base face at angles of 10°, 15° and 20°. In the case of the bonding pattern of the protrusion, as shown in table 2 and FIG. 11, when the bonding pattern such as the protrusions is formed on the base face by irradiating the laser beam at an angle of 10° with respect to the base face, the average adhesive strength is 13.11 Mpa (137.68N), which indicates that the adhesive strength of the adhesive is strongest.

TABLE 3

(Adhesive strength of bonding pattern of hole according to irradiation angle of laser beam)

| NO. of test | Bonding pattern of hole (10°) | | Bonding pattern of hole (15°) | | Bonding pattern of hole (20°) | |
| --- | --- | --- | --- | --- | --- | --- |
| | Unit: N | Unit: MPa | Unit: N | Unit: MPa | Unit: N | Unit: MPa |
| 1 | 66.2 | 6.30 | 231 | 22.00 | 376.7 | 35.88 |
| 2 | 89.6 | 8.53 | 251.2 | 23.92 | 185 | 17.62 |
| 3 | 83.7 | 7.97 | 159.3 | 15.17 | 245.8 | 23.41 |
| 4 | 87.3 | 8.31 | 160.4 | 15.28 | 94.4 | 8.99 |
| 5 | 136.2 | 12.97 | 226.3 | 21.55 | 136.5 | 13.00 |
| 6 | 60.1 | 5.72 | 271.3 | 25.84 | 318.7 | 30.55 |
| 7 | 57.5 | 5.48 | 238 | 22.67 | 229.9 | 21.90 |
| 8 | 90.4 | 8.61 | 288.9 | 27.51 | — | 0.00 |
| 9 | 75.2 | 7.16 | 195.6 | 18.63 | 212.3 | 20.22 |
| 10 | 74 | 7.05 | 246.6 | 23.49 | 308.2 | 29.35 |
| 11 | 70.1 | 6.68 | 235.2 | 22.40 | 220.9 | 21.04 |
| 12 | 122.4 | 11.66 | 172.8 | 16.46 | 213.6 | 20.34 |
| 13 | 103.3 | 9.84 | 242.6 | 23.10 | 133.3 | 12.70 |
| 14 | 89.5 | 8.52 | 169.6 | 16.15 | 201.8 | 20.08 |
| 15 | 76.7 | 7.30 | 174.9 | 16.66 | 214.4 | 20.42 |
| Average | 85.48 | 8.14 | 217.58 | 20.72 | 221.4643 | 21.09 |

Figure 12:
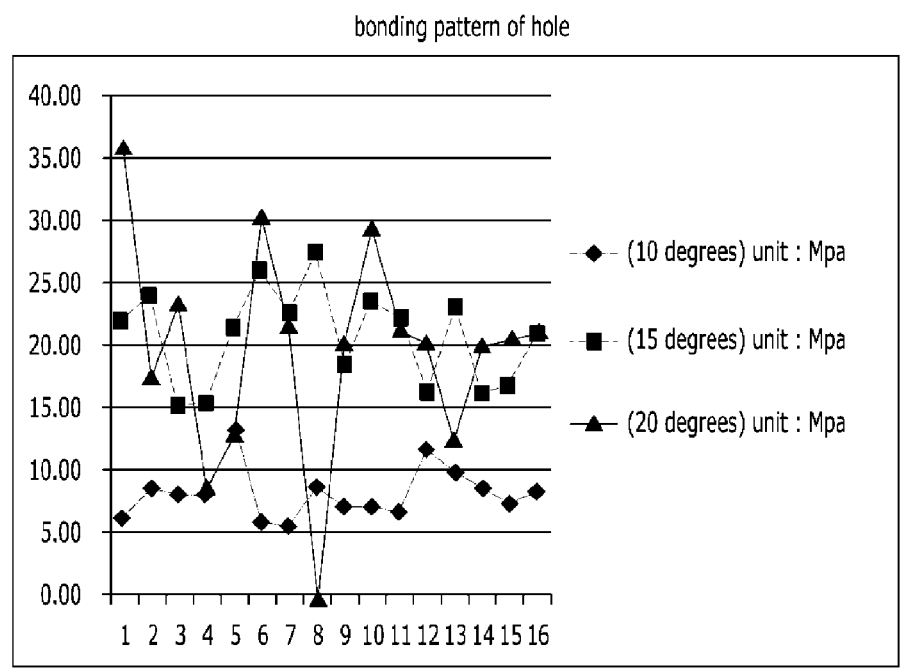

As shown in FIGS. 8 and 9, the bonding pattern such as the holes is formed on the base face by irradiating the laser beam onto the base face at angles of 10°, 15° and 20°. In the case of the bonding pattern of the holes, as shown in table 3 and FIG. 12, when the bonding pattern such as the holes is formed on the base face by irradiating the laser beam at an angle of 20° with respect to the base face, the average adhesive strength is 21.09 Mpa (221.4643N), which indicates that the adhesive strength of the adhesive is strongest.

Sixth Embodiment

Adhesive Strength of Each Bonding Pattern According to Water Spray

TABLE 4

| NO. of test | Bonding pattern of hole | | Bonding pattern of protrusion | | Bonding pattern of dent line | |
|---|---|---|---|---|---|---|
| | Unit: N | Unit: MPa | Unit: N | Unit: MPa | Unit: N | Unit: MPa |
| 1 | 69 | 6.57 | 116.5 | 11.10 | 152.9 | 14.56 |
| 2 | 92 | 8.76 | 21.3 | 2.03 | 187.3 | 17.84 |
| 3 | 83.6 | 7.96 | 21.1 | 2.01 | 88.2 | 8.40 |
| 4 | 91.4 | 8.70 | 90.2 | 8.59 | 174.1 | 16.58 |
| 5 | 136.5 | 13.00 | 117.3 | 11.17 | 199 | 18.95 |
| 6 | 118.1 | 11.25 | 121.6 | 11.58 | 131.7 | 12.54 |
| 7 | 52.1 | 4.96 | 58.9 | 5.61 | 117.8 | 11.2 |
| 8 | 96.3 | 9.17 | 72.1 | 6.87 | 168.5 | 16.05 |
| 9 | 95.2 | 9.07 | 114.5 | 10.90 | 72.8 | 6.93 |
| 10 | 113.3 | 10.79 | 49.1 | 4.68 | 123.1 | 11.72 |
| 11 | 46.6 | 4.44 | 110.3 | 10.50 | 238.5 | 22.71 |
| 12 | 99.6 | 9.49 | 134.4 | 12.80 | 191.1 | 18.20 |
| 13 | 98.9 | 9.42 | 25.2 | 2.40 | 133.9 | 12.75 |
| 14 | 39.9 | 3.80 | 120.2 | 11.45 | 190.8 | 18.17 |
| 15 | 56.2 | 5.35 | 100.7 | 9.59 | 136.7 | 13.02 |
| Average | 92.05 | 8.77 | 84.89333 | 8.09 | 153.76 | 14.64 |

As shown in FIGS. 8 and 9, while the hole bonding pattern, protrusion bonding pattern, and dent line bonding pattern are processed by irradiating the laser beam onto the base face, water as a cutting material is sprayed to cool the heat generated in the processed portion of the base face. As a result of the processing of the bonding pattern having been performed while water is sprayed, as shown in Table 4, the dent line bonding pattern among the bonding patterns has the adhesive strength of 14.64 Mpa (153.76N) on an average, which indicates that the adhesive strength of the adhesive is strongest.

In the foregoing, the invention has been described in detail with reference to preferred embodiments thereof. However, it will be appreciated by those skilled in the art that modifications and changes may be made in these embodiments without departing from the principles and spirit of the invention, the scope of which is defined in the appended claims and their equivalents.

DESCRIPTION OF REFERENCE NUMERALS

| | |
|---|---|
| 1: tooth | 2: rubber ring |
| 3: wire | 11: base face |
| 12: slot | 13: first wing |
| 14: second wing | 15: first side face groove |
| 16: second side face groove | |
| 17: wing division groove | |
| 18: coupling groove | 20: bonding pattern |
| 21: dent line | 22: protrusion |
| 23: dent face | 24: hole |
| 30: laser beam apparatus for processing | |
| 31: laser beam | 32: processing table |
| 33: cutting material | S100: first step |
| S200: second step | |

What is claimed is:

1. A manufacturing method of an orthodontic bracket including a base face, which is formed at one side of the orthodontic bracket, coated with an adhesive for attachment to teeth to attach the orthodontic bracket to teeth; a bonding pattern that is formed on the base face by irradiating a laser beam onto the base face at a vertical angle or at a predetermined angle with respect to the base face so that the adhesive for attachment to teeth permeates the bonding pattern to hold the base face on thereby allowing the bracket to be fixed securely to the teeth; a slot into which a wire is inserted along a longitudinal direction at the center of a face of the orthodontic bracket, opposite to the base face; wings formed with a first wing and a second wing formed at both side faces of the orthodontic bracket; first side face groove and second side face groove that are formed oppositely each other at the centers of both side faces of the orthodontic bracket so as to divide the wings and the base face so that a rubber ring is inserted thereto in order for the wire inserted into the slot not to get out of the slot; a wing division groove that is formed, at a right angle to the slot, on a face center on which the slot of the orthodontic bracket is formed so that the first wing and the second wing are divided into two, respectively, thereby each being provided with a pair of the first wing and second wing; and a coupling groove provided at one end of the first wing of right side so that a rubber ring is coupled correspondingly thereto in state where the first wing of right side is formed longer than the first wing of left side among the pair of the first wings of right and left sides formed by the wing division groove, the method comprising:

a first step of setting, in a laser beam apparatus, an irradiation angle of the laser beam relative to the base face, an irradiation depth of the laser beam relative to the base face and a bonding pattern shape of the base face to be processed, the bonding pattern being set in such a manner that holes are formed throughout the base face; and a second step of forming the bonding pattern on the base face by irradiating the laser beam from the laser beam apparatus onto the base face at a right angle or a predetermined angle with respect to the base face according to the irradiation angle of the laser beam relative to the base face, the irradiation depth of the laser beam relative to the base face and the bonding pattern shape of the base face to be processed, which are set in the laser beam apparatus, the irradiation angle of the laser beam being 20 degrees relative to the base face, in order to form the bonding pattern on the base face of the orthodontic bracket.

2. The manufacturing method of an orthodontic bracket according to claim 1, wherein the cutting material is any one selected from water, hand cream, and cutting oil.

3. The manufacturing method of an orthodontic bracket according to claim 1, wherein the bonding pattern formed on the base face is in a shape of being formed with dent lines formed in a line throughout the base face.

4. The manufacturing method of a orthodontic bracket of claim 1, wherein the holes have any one shape selected from a group consisting of circular, square, star, and hexagonal shapes.

* * * * *